(12) United States Patent
Lambert et al.

(10) Patent No.: US 11,337,936 B2
(45) Date of Patent: *May 24, 2022

(54) AMPHETAMINE TRANSDERMAL COMPOSITIONS WITH ACRYLIC BLOCK COPOLYMER

(71) Applicant: Noven Pharmaceuticals, Inc., Miami, FL (US)

(72) Inventors: Robert Lambert, Miami, FL (US); Weijun Lu, Miami, FL (US); Jun Liao, Miami, FL (US)

(73) Assignee: NOVEN PHARMACEUTICALS, INC., Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/206,369

(22) Filed: Mar. 12, 2014

(65) Prior Publication Data

US 2014/0271865 A1    Sep. 18, 2014

Related U.S. Application Data

(60) Provisional application No. 61/785,298, filed on Mar. 14, 2013.

(51) Int. Cl.
*A61K 31/137* (2006.01)
*A61K 9/70* (2006.01)

(52) U.S. Cl.
CPC .......... *A61K 31/137* (2013.01); *A61K 9/7061* (2013.01)

(58) Field of Classification Search
None
See application file for complete search history.

(56) References Cited

U.S. PATENT DOCUMENTS

| | | | |
|---|---|---|---|
| 5,234,957 A | 8/1993 | Mantelle | |
| 5,332,576 A | 7/1994 | Mantelle et al. | |
| 5,446,070 A | 8/1995 | Mantelle | |
| 5,719,197 A | 2/1998 | Kanios et al. | |
| 5,958,446 A | 9/1999 | Miranda et al. | |
| 6,024,974 A | 2/2000 | Li | |
| 6,024,976 A | 2/2000 | Miranda | |
| 6,210,705 B1 | 4/2001 | Mantelle et al. | |
| 6,235,306 B1 | 5/2001 | Miranda et al. | |
| 6,316,022 B1 | 11/2001 | Mantelle et al. | |
| 6,348,211 B1 | 2/2002 | Mantelle et al. | |
| 6,562,363 B1 | 5/2003 | Mantelle et al. | |
| 7,846,916 B2 | 12/2010 | Houze | |
| 7,867,986 B2 | 1/2011 | Houze | |
| 7,879,831 B2 | 2/2011 | Houze | |
| 7,989,496 B2 | 8/2011 | Hartwig et al. | |
| 7,993,671 B2 | 8/2011 | Mantelle et al. | |
| 8,153,151 B2 | 4/2012 | Houze | |
| 8,187,628 B2 | 5/2012 | Houze | |
| 8,216,606 B2 | 7/2012 | Houze | |
| 8,231,906 B2 | 7/2012 | Mantelle | |
| 8,246,976 B2 | 8/2012 | Nguyen | |
| 8,277,838 B2 | 10/2012 | Nguyen | |
| 8,337,884 B2 | 12/2012 | Mantelle et al. | |
| 8,343,538 B2 | 1/2013 | Kanios et al. | |
| 8,591,941 B2 | 11/2013 | Kanios et al. | |
| 8,632,802 B2 | 1/2014 | Kanios | |
| 8,703,175 B2 | 4/2014 | Kanios et al. | |
| 8,715,723 B2 | 5/2014 | Kanios et al. | |
| 8,784,874 B2 | 7/2014 | Strauss | |
| 8,784,877 B2 | 7/2014 | Houze et al. | |
| 2006/0173124 A1* | 8/2006 | Paul | C08F 293/005 524/558 |
| 2011/0129535 A1 | 6/2011 | Mantelle | |
| 2011/0160245 A1 | 6/2011 | Mantelle et al. | |
| 2011/0288124 A1 | 11/2011 | Mantelle et al. | |
| 2013/0156815 A1 | 6/2013 | Mantelle | |
| 2013/0317461 A1 | 11/2013 | Kanios et al. | |
| 2013/0324575 A1 | 12/2013 | Mantelle et al. | |
| 2014/0105979 A1 | 4/2014 | Liao et al. | |
| 2014/0121611 A1 | 5/2014 | Lambert et al. | |
| 2014/0179739 A1 | 6/2014 | Mantelle et al. | |
| 2014/0182597 A1 | 7/2014 | Patel et al. | |
| 2014/0186424 A1 | 7/2014 | Kulakofsky et al. | |
| 2014/0188056 A1 | 7/2014 | Mori et al. | |
| 2014/0200530 A1 | 7/2014 | Mantelle | |
| 2014/0243764 A1 | 8/2014 | Kanios et al. | |
| 2014/0248330 A1 | 9/2014 | Kanios | |
| 2014/0271792 A1 | 9/2014 | Liao | |
| 2014/0276479 A1 | 9/2014 | Nguyen et al. | |
| 2014/0276483 A1 | 9/2014 | Liao et al. | |
| 2014/0288038 A1 | 9/2014 | Kanios et al. | |

FOREIGN PATENT DOCUMENTS

WO    WO 00/59479    10/2000

OTHER PUBLICATIONS

International Search Report dated Aug. 13, 2014 in application No. PCT/US2014/024281.
U.S. Appl. No. 14/208,367, filed Mar. 13, 2014, Nguyen et al.
U.S. Appl. No. 13/616,919, filed Sep. 14, 2012, Houze et al.
U.S. Appl. No. 14/208,348, filed Mar. 13, 2014, Liao et al.
Cilurzo et al., "Adhesive properties: a critical issue in transdermal patch development," Expert Opinion on Drug Delivery, (2012) vol. 9, No. 1, pp. 33-45, DOI: 10.1517/17425247.2012.637107 (Published online Dec. 2011).
Remington: The Science and Practice of Pharmacy, "Medicated Topicals," p. 936 (22nd ed., 2013).

* cited by examiner

*Primary Examiner* — David J Blanchard
*Assistant Examiner* — Daniel F Coughlin
(74) *Attorney, Agent, or Firm* — Foley & Lardner LLP

(57) ABSTRACT

Described are transdermal drug delivery compositions comprising amphetamine, methods of making them and therapeutic methods using them. The compositions are provided in a flexible, finite form (e.g. "patch"-type systems) and comprise a polymer matrix that includes amphetamine and an acrylic block copolymer.

14 Claims, 3 Drawing Sheets

AMPHETAMINE TRANSDERMAL COMPOSITIONS WITH ACRYLIC BLOCK COPOLYMER

CROSS-REFERENCE TO RELATED APPLICATIONS

This application claims the benefit under 35 U.S.C. § 119(e) to U.S. provisional application 61/785,298, filed Mar. 14, 2013, the contents of which are incorporated here by reference in their entirety.

FIELD

The present invention relates generally to the transdermal delivery of amphetamine, transdermal drug delivery compositions comprising amphetamine, methods of making them and therapeutic methods using them. Transdermal drug delivery compositions comprising amphetamine are useful for transdermally delivering amphetamine, such as may be desired for achieving central nervous system stimulation, for the treatment of Attention Deficit Disorder (ADD) and/or Attention Deficit/Hyperactivity Disorder (ADHD), and/or for the treatment of narcolepsy.

BACKGROUND

Many factors influence the design, manufacture, and performance of transdermal drug delivery compositions. These include the individual drugs themselves, the physical and chemical characteristics of the compositions' components and their performance and behavior relative to other components, external and environmental conditions during manufacturing and storage, properties of the application site, the desired rate of drug delivery and therapeutic onset, the desired drug delivery profile, and the intended duration of delivery, among others.

Compositions for the transdermal delivery of amphetamine are known, but there remains a need for compositions that exhibit good physical properties, such a good shear and cohesion properties, while still achieving good drug flux.

SUMMARY

Some embodiments relate to compositions for the transdermal delivery of amphetamine in the form of a flexible finite system for topical application, comprising a polymer matrix comprising amphetamine or a pharmaceutically acceptable salt or prodrug thereof, wherein the polymer matrix comprises an acrylic block copolymer. In some embodiments, the acrylic block copolymer is made from one or more monomers selected from the group consisting of methyl acrylate, methyl methacrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, and acryl amide. In some embodiments, the acrylic block copolymer comprises one or more of poly (butyl acrylate), poly(methyl methacrylate), methyl methacrylate/butyl acrylate (MMA/BA) blocks, and methyl methacrylate/butyl acrylate/alpha methyl styrene/polypropylene glycol (MMA/BA/AMS/PPG) blocks. In some embodiments, the polymer matrix comprises from about 20% to about 80% by weight acrylic block copolymer, or from about 25% to about 65% by weight acrylic block copolymer.

In some embodiments, the polymer matrix further comprises a random acrylic polymer. In some embodiments, the random acrylic polymer is made from one or more monomers selected from the group consisting of butyl acrylate, methyl acrylate, acrylic acid, ethyl hexyl acrylate, and hydroxy ethyl acrylate. In some embodiments, the random acrylic polymer is made from one or more monomers selected from the group consisting of ethyl hexyl acrylate, methyl acrylate, butyl acrylate, and octyl acrylamide. In some embodiments, the polymer matrix comprises from about 10% to about 55% by weight random acrylic polymer, or from about 20% to about 30% by weight random acrylic polymer.

In accordance with any embodiments, the amphetamine may be amphetamine free base. In some embodiments, the polymer matrix comprises from about 10% to about 20% by weight amphetamine free base.

In accordance with some embodiments, the composition is capable of delivering amphetamine over a period of time of from about 6 to about 12 hours, such as up to about 10 hours.

In some embodiments, the composition further comprises a backing layer and/or a release liner.

In some embodiments, the composition is for the transdermal delivery of amphetamine, or for achieving central nervous system stimulation or treating of Attention Deficit Disorder (ADD), Attention Deficit/Hyperactivity Disorder (ADHD), or narcolepsy. Also provided are methods for the transdermal delivery of amphetamine, or for achieving central nervous system stimulation or treating Attention Deficit Disorder (ADD), Attention Deficit/Hyperactivity Disorder (ADHD), or narcolepsy, comprising topically applying a composition as described herein to the skin or mucosa of a subject in need thereof. Also provided are uses of amphetamine in the preparation of a medicament in the form of a composition as described herein for transdermally delivering amphetamine to the skin or mucosa of a subject in need thereof, or for achieving central nervous system stimulation or treating Attention Deficit Disorder (ADD), Attention Deficit/Hyperactivity Disorder (ADHD), or narcolepsy.

Also provided are methods of manufacturing a composition for the transdermal delivery of amphetamine in the form of a flexible finite system for topical application, comprising forming a polymer matrix blend comprising an acrylic block copolymer and amphetamine or pharmaceutically acceptable salt or prodrug thereof in a solvent, applying the polymer matrix blend to a support layer, and removing any remaining solvent.

DETAILED DESCRIPTION

Figure 1:
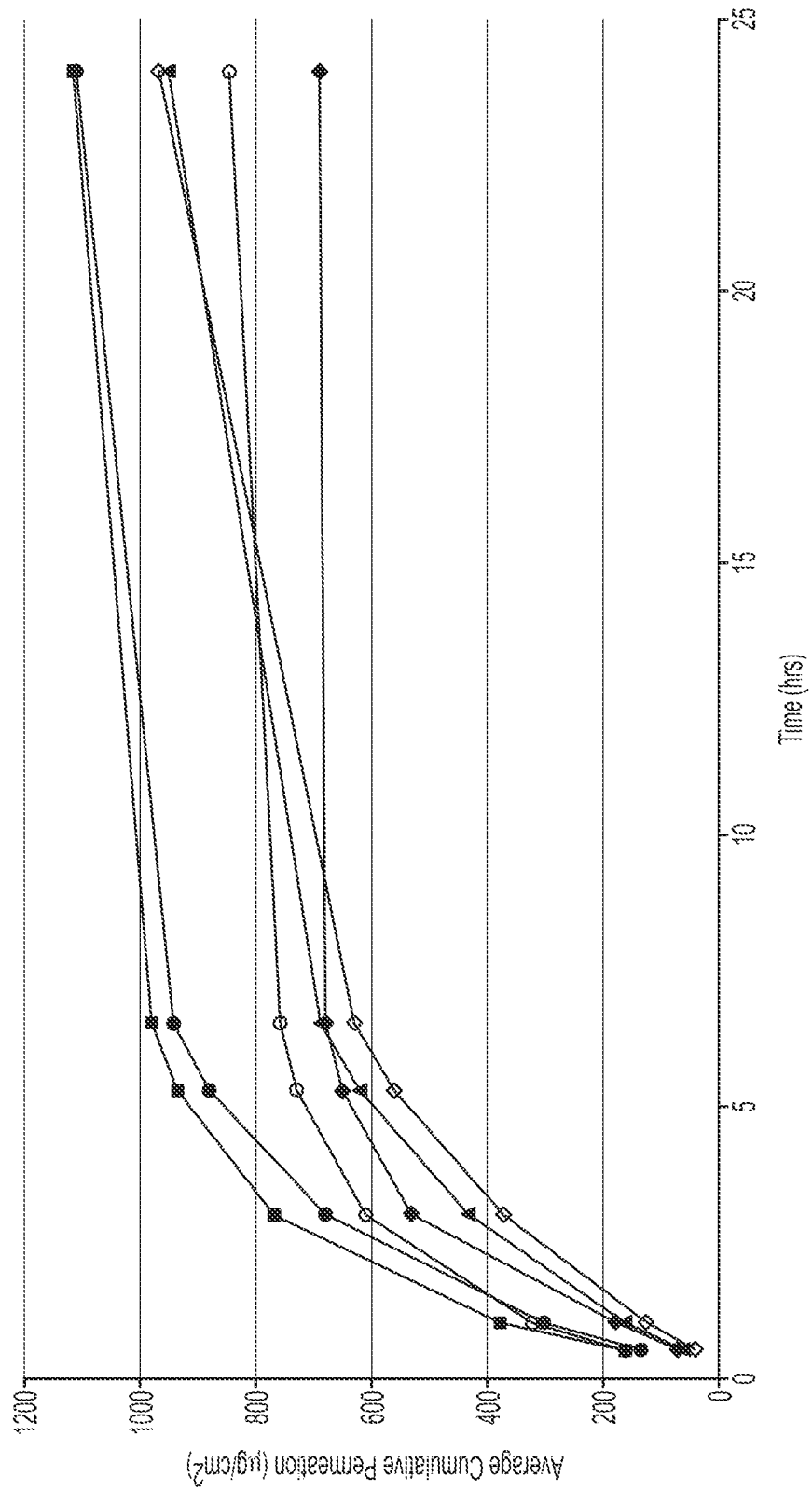
FIG. 1 illustrates the cumulative drug flux ($\mu g/cm^2$) from compositions as described herein and a comparison composition over 24 hours, as described in Example 1.

Described herein are transdermal drug delivery compositions comprising amphetamine, methods of making them and therapeutic methods using them. The compositions are provided in a flexible, finite form (e.g., "patch"-type systems) and comprise a polymer matrix that includes amphetamine and an acrylic block copolymer.

Definitions

Technical and scientific terms used herein have the meanings commonly understood by one of ordinary skill in the art to which the present invention pertains, unless otherwise defined. Reference is made herein to various methodologies known to those of ordinary skill in the art. Publications and other materials setting forth such known methodologies to which reference is made are incorporated herein by reference in their entireties as though set forth in full. Any suitable materials and/or methods known to those of ordinary skill in the art can be utilized in carrying out the present invention. However, specific materials and methods are described. Materials, reagents and the like to which reference is made in the following description and examples are obtainable from commercial sources, unless otherwise noted.

As used herein, the singular forms "a," "an," and "the" designate both the singular and the plural, unless expressly stated to designate the singular only.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

The phrase "substantially free" as used herein means that the described composition (e.g., polymer matrix, etc.) comprises less than about 5%, less than about 3%, or less than about 1% by weight, based on the total weight of the composition at issue, of the excluded component(s).

The phrase "free of" as used herein means that the described composition (e.g., polymer matrix, etc.) is formulated without adding the excluded component(s) as an intended component, although trace amounts may be present in other components or as a by-product or contaminant, such that the composition comprises at most only trace amounts of the excluded component(s).

As used herein "subject" denotes any mammal in need of drug therapy, including humans. For example, a subject may be suffering from or at risk of developing a condition that can be treated or prevented with amphetamine (such as ADD or ADHD or narcolepsy), or may be taking amphetamine for other purposes.

As used herein, the terms "topical" and "topically" mean application to a skin or mucosal surface of a mammal, while the terms "transdermal" and "transdermal" connote passage through the skin or mucosa (including oral, buccal, nasal, rectal and vaginal mucosa), into systemic circulation. Thus, the compositions described herein may be applied topically to a subject to achieve transdermal delivery of amphetamine.

As used herein, the phrases "therapeutically effective amount" and "therapeutic level" mean that drug dosage or plasma concentration in a subject, respectively, that provides the specific pharmacological effect for which the drug is administered in a subject in need of such treatment. It is emphasized that a therapeutically effective amount or therapeutic level of a drug will not always be effective in treating the conditions/diseases described herein, even though such dosage is deemed to be a therapeutically effective amount by those of skill in the art. For convenience only, exemplary dosages, drug delivery amounts, therapeutically effective amounts and therapeutic levels are provided below with reference to adult human subjects. Those skilled in the art can adjust such amounts in accordance with standard practices as needed to treat a specific subject and/or condition/disease.

As noted above, the compositions described herein are in a "flexible, finite form." As used herein, the phrase "flexible, finite form" means a substantially solid form capable of conforming to a surface with which it comes into contact, and capable of maintaining contact so as to facilitate topical application. Such systems in general are known in the art and commercially available, such as transdermal drug delivery patches.

The compositions comprise a drug-containing polymer matrix that releases amphetamine upon application to the skin (or any other surface noted above). The compositions in flexible, finite form may have a backing layer in addition to the drug-containing polymer matrix layer. In some embodiments, the compositions in flexible, finite form may have a release liner layer in addition to a drug-containing polymer matrix layer and backing layer.

As used herein, "drug-containing polymer matrix" refers to a polymer composition which contains one or more drugs, such as amphetamine, and a polymer, such as a pressure-sensitive adhesive polymer or a bioadhesive polymer. A polymer is an "adhesive" or "bioadhesive" if it has the properties of adhesiveness per se. Other polymers can function as an adhesive or bioadhesive by the addition of tackifiers, plasticizers, crosslinking agents or other excipients. Thus, in some embodiments, the polymer optionally comprises tackifiers, plasticizers, crosslinking agents or other additives known in the art.

As used herein, the term "pressure-sensitive adhesive" refers to a viscoelastic material which adheres instantaneously to most substrates with the application of very slight pressure and remains permanently tacky. As noted above, a polymer is a pressure-sensitive adhesive polymer if it has the properties of a pressure-sensitive adhesive per se. Other polymers may function as a pressure-sensitive adhesive by admixture with tackifiers, plasticizers or other additives. The term pressure-sensitive adhesive also includes mixtures of different polymers.

In some embodiments, the polymer matrix is a pressure-sensitive adhesive at room temperature and exhibits desirable physical properties, such as good adherence to skin, ability to be peeled or otherwise removed without substantial trauma to the skin, retention of tack with aging, etc. In some embodiments, the polymer matrix has a glass transition temperature ($T_g$), measured using a differential scanning calorimeter, of between about −70° C. and 0° C.

In some embodiments, the compositions in flexible, finite form are "monolithic" or "monolayer" systems, such that the drug-containing polymer matrix layer is the only polymeric layer present other than the backing layer and the release liner, if present. In such embodiments, the polymer matrix functions as both the drug carrier and the means of affixing the system to the skin or mucosa.

Amphetamine

Amphetamine (alpha-methylphenethylamine) is a chiral drug. The commercially available oral amphetamine product Adderall® includes several different amphetamine salts, including amphetamine sulfate, amphetamine saccharate, and amphetamine aspartate monohydrate, in an overall ratio of d-amphetamine to l-amphetamine of 3:1.

The compositions described herein may be formulated with amphetamine free base or any salt of amphetamine, or any prodrug thereof, or any combinations thereof, and with any isomeric content, and any combinations thereof. In specific embodiments, the compositions comprise d-amphetamine. In further specific embodiments the amphetamine component consists essentially of d-amphetamine (e.g., it contains no more than trace amounts of other amphetamine species). In still further specific embodiments the amphetamine component consists of d-amphetamine. In other specific embodiments, the composition comprises a prodrug of d-amphetamine, such as lisdexamfetamine, in the free base or any salt form, such as lisdexamfetamine dimesylate.

In addition to the salts mentioned above, exemplary suitable pharmaceutically acceptable salts of amphetamine are salts of weak inorganic and organic acids, and quaternary ammonium salts.

These include without limitation, salts with acids such as sulfuric, phosphoric, hydrochloric, hydrobromic, hydriodic, sulfamic, citric, lactic, maleic, malic, succinic, tartaric, cinnamic, acetic, benzoic, gluconic, or ascorbic acid, or quaternary ammonium salts with organic esters of sulfuric, hydrohalic, or aromatic sulfonic acids, such as methyl chloride, methyl bromide, ethyl chloride, propyl chloride, butyl chloride, isobutyl chloride, benzylchloride, benzyl bromide, phenethyl bromide, naphthymethyl chloride, dimethyl sulfate, methyl benzenesulfonate, ethyl toluenesulfonate, ethylene chlorohydrin, propylene chlorohydrin, allyl bromide, methylallyl bromide or crotyl bromide esters.

The compositions described herein include a therapeutically effective amount of amphetamine and/or pharmaceutically acceptable salt(s) and/or prodrug(s) thereof. Generally, the amount of amphetamine is from about 1% to about 50%, including from about 5% to about 40%, such as from about 10% to about 20% by weight, based on the total dry weight of the polymer matrix. In specific embodiments, the polymer matrix comprises about 15% by weight amphetamine, based on the total dry weight of the polymer matrix. In other specific embodiments, the polymer matrix comprises about 10% by weight amphetamine, based on the total dry weight of the polymer matrix. In other specific embodiments, the polymer matrix comprises about 20% by weight amphetamine, based on the total dry weight of the polymer matrix.

In accordance with any of the embodiments described herein, the composition may include from about 5 to about 30 mg of amphetamine base or an equivalent amount of a pharmaceutically acceptable salt or prodrug thereof, including about 5, 10, 15, 20, 25, or 30 mg of amphetamine base or equivalent.

Polymer Matrix

The compositions described herein comprise a polymer matrix that comprises, consists essentially of, or consists of amphetamine and/or pharmaceutically acceptable salt(s) thereof and at least one polymer.

In some embodiments, the compositions comprise amphetamine free base, which is a liquid drug. In these embodiments, the liquid, non-viscous nature of the drug tends to undermine the physical properties of the composition, particularly at high drug loads, such as at or about 10% by weight drug. For example, polymer compositions comprising liquid drug have a high propensity to exhibit cold flow (e.g., oozing). This propensity increases as the concentration of the liquid drug in the polymer matrix is increased. The liquid drug also impacts other physical properties of the compositions, such as adhesion, cohesion, and tackiness.

In some embodiments, the compositions described herein address the problems associated with formulating liquid drug by using a polymer matrix that comprises an acrylic block copolymer (ABC). While not wanting to be bound by theory, it is believed that the use of an ABC permits a composition with a higher shear force and higher cohesiveness as compared to a composition comprising conventional random acrylic polymers with the same monomeric make-up. This in turn permits higher drug loading in the polymer matrix, which in turn permits the design and use of smaller transdermal drug delivery systems (e.g., systems with a smaller active surface area). This in turn offers advantages in the context of cost savings and improved patient compliance.

In some embodiments, the amphetamine is formulated within the polymer matrix comprising an ABC such that an absorbent layer is not required. Thus, in some embodiments, the transdermal drug delivery systems described herein do not include an absorbent layer, such as an absorbent backing material.

ABCs also offer advantages in the manufacturing/formulation context, as they generally require less processing solvent than a corresponding random acrylic polymer with the same monomer make-up. That is, they reach a suitable (reduced) viscosity with a lower amount of solvent than a corresponding random acrylic polymer with the same monomer make-up.

As noted above, when amphetamine is formulated in a polymer matrix comprising an ABC, the resulting compositions exhibit a greater drug flux than a corresponding composition formulated with a random acrylic polymer with the same monomer make-up. Therefore, in some embodiments, compositions as described herein achieve greater drug flux from a composition comprising the same amount of drug, as compared to a corresponding composition formulated with a random acrylic polymer with the same monomer make-up. Further, in some embodiments, compositions as described herein achieve delivery of a target amount of drug in a shorter period of time, as compared to a corresponding composition formulated with a random acrylic polymer with the same monomer make-up. This offers several advantageous design options, such as one or more of the use of a smaller system (e.g., a smaller patch, with a smaller active surface area) and/or a shorter application period, and offers several benefits such as reduced risk of local skin irritation and/or reduced risk of systemic side effects. Further, in some embodiments, the compositions as described herein reach completion of drug delivery in a shorter period of time, and so can be administered without a mandatory rest period in between applications of subsequent systems. For example, in some embodiments, the compositions as described herein deliver amphetamine over a period of time of up to about 10 hours, such for about 4 to about 10 hours.

In some embodiments, the compositions described herein comprise a polymer matrix that includes a single ABC or a mixture of ABCs. In other embodiments, the polymer matrix comprises one or more ABCs and one or more random acrylic polymers. The type(s), amount(s), and, if applicable, relative amounts(s) of the polymer(s) used in the polymer matrix can be selected to achieve a composition with desired physical and pharmacokinetic properties, as discussed above and below and illustrated in the examples.

Acrylic Block Copolymers

As noted above, in some embodiments the polymer matrix comprises one or more acrylic block copolymers (ABCs), such as one or more pressure-sensitive adhesive acrylic block copolymers.

The ABC can be comprised of any acrylic monomer(s) and monomer configuration(s) that are compatible with methylphenidate (as discussed above) that result in a matrix with suitable physical and pharmacokinetic properties.

Acrylate monomers which can be used include alkyl acrylates and alkyl methacrylates, such as methyl acrylate, methyl methacrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, and octyl acrylamide. In some embodiments, the ABC is comprised of methyl methacrylate/butyl acrylate (MMA/BA) blocks. In some embodiments, the ABC is comprised of methyl methacrylate/butyl acrylate/alpha methyl styrene/polypropylene glycol (MMA/BA/AMS/PPG) blocks. In some embodiments, the ABC comprises poly(butyl acrylate) and/or poly(methyl methacrylate). Suitable acrylic block copolymers are available commercially, such as from Henkel North America, e.g., Duro-Tak® 87-9900.

In any embodiments, the ABC polymer may comprise a mixture of two or more ABC in any relative amounts. In some embodiments, the types and amounts of polymers comprising each ABC are selected and controlled to achieve an ABC that exhibits and confers desired physical properties. For example, in some embodiments, the ABC includes poly(butyl acrylate) and poly(methyl methacrylate).

The ABC may be present in any amount. In some embodiments, the ABC is present in an amount effective to achieve one or more of the beneficial effects discussed herein, such as improved shear properties, improved adhesion properties, enhanced drug flux, etc. In some embodiments, the ABC comprises from about 1% to about 99% by weight of the polymer matrix, including from about 5% to about 95%, from about 10% to about 90%, from about 20% to about 80%, and from about 25% to about 75%, such as about 25%, about 28%, about 30%, about 35%, about 40%, about 42.5%, about 45%, about 50%, about 55%, about 60%, and about 65%.

Random Acrylic Polymer

In some embodiments, the polymer matrix further comprises a random acrylic polymer. As used herein, the term "random" as modifying "polymer" is used in contrast to block copolymers, and refers to acrylic polymers that have a random arrangement of monomer units.

In some embodiments, the random acrylic polymer does not contain reactive groups (e.g., the acrylic polymer is a non-reactive acrylic polymer), as discussed above. For example, in some embodiments the acrylic polymer is free of vinyl acetate groups. Examples of such acrylic polymers include acrylic polymers made from butyl acrylate monomers, butyl methacrylate monomers, methyl acrylate monomers, methyl methacrylate monomers, ethyl hexyl acrylate monomers, and/or hydroxy ethyl acrylate monomers, as well as methacrylic acid, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, and tridecyl methacrylate. In specific embodiments, the acrylic polymer is made from one or more of ethyl hexyl acrylate, methyl acrylate, butyl acrylate, and octyl acrylamide monomers. In further specific embodiments, the acrylic polymer is made from each of ethyl hexyl acrylate, methyl acrylate, butyl acrylate, and octyl acrylamide monomers. In further specific embodiments, the polymer matrix includes two or more acrylic polymer that each are made from one or more of ethyl hexyl acrylate, methyl acrylate, butyl acrylate, and octyl acrylamide monomers. Suitable acrylic polymers can be obtained commercially or by polymerizing or copolymerizing suitable monomers such as acrylic monomers and other polymerizable monomers, such as those set forth above.

Acrylate monomers which can be used include butyl acrylate, butyl methacrylate, methyl acrylate, methyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, and tridecyl methacrylate. In specific embodiments, the acrylic polymer includes methacrylate monomers and 2-ethylhexyl acrylate monomers. In other specific embodiments the acrylic polymer includes methacrylate monomers, 2-ethylhexyl acrylate monomers, and amide-group containing monomers such as octylacrylamide.

Suitable random acrylic polymers which are commercially available include those sold by Henkel North America under the Duro-Tak® brand name such as Duro-Tak® 87-900A, 87-901A, 87-9085, 87-9088, 87-9301A, and by Cytec Industries Inc. under the Gelva® GMS brand name, such as Gelva® GMS 3067, 3071, 3083, 3087 and 3235. Other suitable acrylic polymers are known in the art. See, e.g., the non acid-functional acrylic polymers described in Satas, "Acrylic Adhesives, HANDBOOK OF PRESSURE-SENSITIVE ADHESIVE TECHNOLOGY, 2nd ed., pp. 396-456 (D. Satas, ed.), Van Nostrand Reinhold, N.Y. (1989); Acrylic and Methacrylic Ester Polymers," POLYMER SCIENCE AND ENGINEERING, Vol. 1, 2nd ed., pp 234-268, John Wiley & Sons, (1984).

In any embodiments, the random acrylic polymer may comprise a mixture of two or more random acrylic polymers in any relative amounts. In some embodiments, the type(s) and amount(s) of non-reactive random acrylic polymer(s) is selected to achieve a composition with desired physical or pharmacokinetic properties.

The random acrylic polymer may be present in any amount. In some embodiments, the random acrylic polymer is present in an amount effective to enhance the physical properties of the composition, enhance the drug solubility in the composition, and/or modulate drug flux, etc. In some embodiments, the random acrylic comprises from about 1% to about 60% by weight of the polymer matrix, including from about 10% to about 55%, and from about 20% to about 50%, such as about 20%, about 25%, about 30%, about 35%, about 40%, about 42.5%, about 45%, about 50%, about 55%, and about 57%.

Rubber-Based Polymers

In some embodiments, the polymer matrix further comprises, in addition to the ABC, and additionally or alternatively, the random acrylic polymer, a rubber-based polymer, such as a rubber-based adhesive polymer. Examples of suitable rubber-based polymers include polyisobutylene polymers and styrene-isoprene-styrene block copolymers.

Polyisobutylene polymers suitable for use in polymer matrix compositions are known and are available commercially, and include those sold by BASF under the Oppanol® B brand, which is a series of medium and high molecular weight polyisobutylene polymers having a weight-average molecular weight (Mw) between 40,000 and 4,000,000, and include Oppanol® B100 and Oppanol® B11SFN. In some embodiments, the polymer matrix comprises two or more polyisobutylene polymers of different molecular weights. In accordance with these embodiments, the relative amounts of polyisobutylene polymers can be selected and tailored to produce a product with satisfactory physical and pharmacokinetic properties.

Styrene-isoprene-styrene block copolymers suitable for use in a polymer matrix of transdermal drug delivery compositions are known, and include those sold by Kraton Polymers US under the Kraton® brand name, such as Kraton® D1111 KT.

In some embodiments, the polymer matrix includes a silicone polymer, also referred to as a siloxane or polysiloxane. Silicone polymers used in polymer matrices of transdermal drug delivery compositions are known, In some embodiments, the polymer matrix does not include a silicone polymer, e.g., it is substantially free of or free of silicone polymers, e.g., it is formulated without any silicone polymers.

When the polymer matrix comprises any one or more of these polymers, each polymer can be included in any amount. The relative amounts of each polymer can be selected and tailored to achieve desired physical properties (e.g., strength, tackiness, peel strength, etc.), desired drug solubility/drug loading, and/or desired pharmacokinetic properties (e.g., onset and duration of drug delivery and drug delivery profile, etc.).

Other Components

The polymer matrix of the compositions described herein optionally may further comprise other components typically used in a transdermal drug delivery composition, such as skin permeation enhancers, tackifiers, plasticizers, cross-linking agents or other excipients known in the art.

Although amphetamine base does not generally require a penetration enhancer, in some embodiments, the polymer matrix comprises a penetration enhancer. A "penetration enhancer" is an agent known to accelerate the delivery of the drug through the skin. These agents also have been referred to as accelerants, adjuvants, and sorption promoters, and are collectively referred to herein as "enhancers." This class of agents includes those with diverse mechanisms of action, including those which have the function of improving percutaneous absorption, for example, by changing the ability of the stratum corneum to retain moisture, softening the skin, improving the skin's permeability, acting as penetration assistants or hair-follicle openers or changing the state of the skin including the boundary layer. In some embodiments, the penetration enhancer does not include a reactive moiety, such as an acetyl moiety. a vinyl acetate moiety, an acyl halide moiety, a carbonate ester moiety, a carboxyl moiety, or an ester moiety.

Illustrative penetration enhancers include but are not limited to polyhydric alcohols such as dipropylene glycol, propylene glycol, and polyethylene glycol; oils such as olive oil, squalene, and lanolin; fatty ethers such as cetyl ether and oleyl ether; fatty acid esters such as isopropyl myristate; urea and urea derivatives such as allantoin which affect the ability of keratin to retain moisture; polar solvents such as dimethyidecylphosphoxide, methyloctylsulfoxide, dimethyllaurylamide, dodecylpyrrolidone, isosorbitol, dimethylacetonide, dimethylsulfoxide, decylmethylsulfoxide, and dimethylformamide which affect keratin permeability; salicylic acid which softens the keratin; amino acids which are penetration assistants; benzyl nicotinate which is a hair follicle opener; and higher molecular weight aliphatic surfactants such as lauryl sulfate salts which change the surface state of the skin and drugs administered. Other agents include oleic and linoleic acids, ascorbic acid, panthenol, butylated hydroxytoluene, tocopherol, tocopheryl acetate, tocopheryl linoleate, propyl oleate, and isopropyl palmitate.

In some embodiments, the polymer matrix does not comprise a penetration enhancer.

When present, a penetration enhancer typically is used in an amount up to about 30% by dry weight of the polymer matrix, including up to 30% by weight, up to about 20% by weight, including 20% by weight, or up to about 10% by weight, up to 10% by weight, or up to 5% by weight, including up to 5% by weight, based on the dry weight of the polymer matrix.

Amphetamine contains a primary amine group which is subject to oxidization in the presence of an oxidizing agent such as oxygen. This can result in the formation of undesired compounds during processing and/or storage, such as phenyl acetone. The oxidation of amphetamine can be reduced, minimized or prevented by including an antioxidant in the polymer matrix. In some embodiments, the antioxidant is butylhydroxytoluene (BHT) and/or butylhydroxyanisole (BHA). In other embodiments, the antioxidant is, additionally or alternatively, alpha tocopherol, ascorbic acid, ascorbyl palmitate, propyl gallate, fumaric acid, malic acid, sodium ascorbate, sodium metabisulfite, and the like. In specific embodiments, the antioxidant does not include a reactive moiety, such as such as an acetyl moiety, a vinyl acetate moiety, an acyl halide moiety, a carbonate ester moiety, a carboxyl moiety, or an ester moiety. In specific embodiments, the antioxidant (or combinations thereof) are used in a total amount of from about 0.01 to about 5.0% by weight, including from about 0.1 to about 1.0% by weight, such as about 0.1% by weight, about 0.25% by weight, and about 0.5% by weight, based on the dry weight of the polymer matrix.

As noted above, the polymer matrix may further comprise various tackifying agents, thickeners, fillers, and other additives or components known for use in transdermal drug delivery systems. These optional components include tackifying agents such as aliphatic hydrocarbons, mixed aliphatic and aromatic hydrocarbons, aromatic hydrocarbons, substituted aromatic hydrocarbons, hydrogenated esters, hydrogenated hydrocarbon resins, styrene-isobutylene-styrene block copolymers, polyterpenes, silicone fluid, mineral oil and hydrogenated wood rosins; binders, such as lecithin which "bind" the other ingredients; rheological agents (thickeners) containing silicone, such as fumed silica, reagent grade sand, precipitated silica, amorphous silica, colloidal silicon dioxide, fused silica, silica gel, quartz and particulate siliceous materials commercially available as Syloid®, Cabosil®, Aerosil®, and Whitelite®, such as for enhancing the uniform consistency or continuous phase of the composition or coating. Other additives and excipients include diluents, stabilizers, fillers, clays, buffering agents, biocides, humectants, anti-irritants, antioxidants, preservatives, plasticizing agents, cross-linking agents, flavoring agents, colorants, pigments and the like. Such substances can be present in any amount sufficient to impart the desired properties to the composition. As noted above, in some embodiments, any such components that are present do not include a reactive moiety, such as an acetyl moiety, a vinyl acetate moiety, an acyl halide moiety, a carbonate ester moiety, a carboxyl moiety.

Such additives or excipients are typically used in amounts totaling up to 50%, including from about 0.1% to about 30%, by weight based on the dry weight of the polymer matrix.

Transdermal Drug Delivery Systems

In embodiments where the polymer matrix comprises a pressure-sensitive adhesive or bioadhesive, the polymer matrix can serve as an adhesive portion of the transdermal drug delivery system (e.g., a reservoir device), or can serve as one or more layers of a multi-layer system. Alternatively, a polymer matrix comprising a pressure-sensitive adhesive or bioadhesive with drug dissolved or dispersed therein can constitute a monolithic transdermal drug delivery system. In embodiments where the polymer matrix does not comprise an adhesive, but instead, for example, comprises a polymeric drug reservoir, it can be used in combination with one or more adhesive layers, or with a surrounding adhesive portion, as is well known to those skilled in the art.

In some embodiments, a transdermal drug delivery system consists essentially of the polymer matrix layer. By "consists essentially of the polymer matrix layer" means that the system does not contain any other layers that affect drug delivery, such as an additional rate-controlling polymer layer, rate-controlling membrane, or drug reservoir layer. It will be understood, however, that the system that consists essentially of the polymer matrix layer may comprise a backing layer and/or release liner.

The transdermal drug delivery system may be of any shape or size suitable for transdermal application.

Backing Layer

The transdermal drug delivery system also may include a drug impermeable backing layer or film. (By "impermeable" to the drug is meant that no substantial amount of drug loss through the backing layer is observed.) In some embodiments, the backing layer is adjacent one face of the polymer matrix layer. When present, the backing layer protects the polymer matrix layer (and any other layers present) from the environment and prevents loss of the drug and/or release of other components to the environment during use. Materials suitable for use as backing layers are well-known known in the art and can comprise films of polyester, polyethylene, vinyl acetate resins, ethylene/vinyl acetate copolymers, polyvinyl chloride, polyurethane, and the like, metal foils, non-woven fabric, cloth and commercially available laminates. A typical backing material has a thickness in the range of 2 to 1000 micrometers. For example, 3M's Scotch Pak™ 1012, 9732, 1109, 9680, 9734, 9700, 9719 or 9722 backing material (a polyester film with an ethylene vinyl acetate copolymer heat seal layer) is useful in the transdermal drug delivery systems described herein. In some embodiments, the backing layer is a polyester backing layer.

Release Liner

The transdermal drug delivery system also may include a release liner, typically located adjacent the opposite face of the system as compared to the backing layer. When present, the release liner is removed from the system prior to use to expose the polymer matrix layer and/or an adhesive layer prior to topical application. Materials suitable for use as release liners are well-known known in the art and include the commercially available products, such as silicone-coated release liners, including Bio-Release® liner and Syl-Off® 7610 (both silicone-based) sold by Dow Corning Corporation and 3M's 1020, 1022, 9744, 9748 and 9749 Scotchpak™ (fluoropolymer coated polyester films).

The transdermal drug delivery system may be packaged or provided in a package, such as a pouchstock material used in the prior art for transdermal drug delivery systems. For example, DuPont's Surlyn® can be used in a pouchstock material.

As noted above, a "monolithic" transdermal drug delivery system may include a backing layer and/or release liner, and may be provided in a package.

Methods of Manufacturing Transdermal Drug Delivery Compositions and Systems

The polymer matrices described herein may be prepared by methods known in the art. For example, the polymer matrix material can be applied to a backing layer and release liner by methods known in the art, and formed into sizes and shapes suitable for use. For example, after the polymer matrix is formed, it may be brought into contact with a support layer, such a releaser liner layer or backing layer, in any manner known to those of skill in the art. Such techniques include calender coating, hot melt coating, solution coating, etc.

For example, a polymer matrix can be prepared by blending the components of the polymer matrix, applying the matrix material to a support layer such as a backing layer or release liner, and removing any remaining solvents. The therapeutically active agents can be added at any stage. In one embodiment, all polymer matrix components, including the therapeutically active agents, are blended together. In another embodiment, the polymer matrix components other than the therapeutically active agents are blended together, and then the therapeutically active agents are dissolved or dispersed therein. The order of steps, amount of ingredients, and the amount and time of agitation or mixing can be determined and optimized by the skilled practitioner. An exemplary general method is as follows:

Appropriate amounts of polymer(s), enhancer(s), and organic solvent(s) are combined and thoroughly mixed together in a vessel.

The formulation is transferred to a coating operation where t is coated onto a protective release liner at a controlled specified thickness.

The coated product is passed through an oven in order to drive off all volatile processing solvents.

The dried product on the release liner is then joined to the backing material and wound into rolls for storage.

Appropriate size and shape "systems" are die-cut from the roll material and then pouched.

Other manufacturing methods are known in the art that are suitable for making the systems described herein.

Therapeutic Methods

The compositions described herein are useful in methods for the transdermal delivery of amphetamine, including in methods for achieving central nervous system stimulation or treating Attention Deficit Disorder (ADD) and/or Attention Deficit/Hyperactivity Disorder (ADHD), and/or narcolepsy. In such embodiments, a composition comprising a therapeutically effective amount of amphetamine as described herein is topically applied to a subject in need thereof.

In some embodiments, the compositions achieve transdermal delivery of amphetamine over a period of time of from about 6 to about 10 hours, although the composition may remain on the application site for a longer period of time. In some embodiments, the compositions deliver amphetamine over a period of time of up to about 10 hours. That is, in some embodiments, the compositions reach substantially complete delivery by about 10 hours, meaning that substantially no additional drug is delivered after about 10 hours, even if some drug remains in the composition.

The compositions described herein achieve a transdermal flux of amphetamine (and/or one or more pharmaceutically acceptable salt(s) thereof) that is sufficient to have a therapeutic effect. As used herein, "flux" (also called "permeation rate") is defined as the absorption of a drug through skin or mucosal tissue, and is described by Fick's first law of diffusion:

$$J = -D(dCm/dx)$$

where J is the flux in cm²/sec, D is the diffusion coefficient of the drug through the skin or mucosa in cm²/sec and dCm/dx is the concentration gradient of the drug across the skin or mucosa.

The following specific examples are included as illustrative of the compositions described herein. These examples are in no way intended to limit the scope of the invention. Other aspects of the invention will be apparent to those skilled in the art to which the invention pertains.

Example 1

Systems were prepared using polymer matrix compositions with the following formulations, with the coat weights and backing materials as indicated:

|  | Formula 1-1 (●) | Formula 1-2 (♦) | Formula 1-3 (○) | Formula 1-4 (■) | Comparison Formula (◇) and (▲) |
|---|---|---|---|---|---|
| Amphetamine | 10 | 15 | 15 | 15 | 15 |
| MMA/BA/AMS/PPG ABC | 30 | 25 | — | — | — |
| Duro-Tak ® 87-9900 | 30 | 30 | 28 | 42.5 | — |
| Gelva ® GMS 3087 | 30 | 30 | — | — | 68 |
| Duro-Tak ® 900A | — | — | 57 | 42.5 | 17 |
| Coat Weight (mg/cm²) | 10.5 | 6.5 | 7.1 | 6.9 | 7 |
| Backing | polyester | polyester | polyester | polyester | polyurethane/polyester |

Drug flux from the systems over 24 hours was assessed in an in vitro assay using human cadaver skin. Results are shown in FIG. 1A (flux, μg/cm²/hr) and FIG. 1B (cumulative flux, μg/cm²). As seen in the figures, compositions as described herein achieve good drug flux, which can be selected and controlled by selecting and controlling the types and amounts of ABC polymer(s) and acrylic polymer(s).

The comparison system in this example includes an absorbent layer (e.g., the polyurethane layer of the backing) as may typically be used to inhibit cold flow. The results show that the comparison system achieves a different drug flux profile than the systems that do not include an absorbent layer.

Example 2

Systems were prepared using polymer matrix compositions with the following formulations, with the coat weights indicated:

|  | Formula 2-1 (▲) | Formula 2-2 (●) | Formula 2-3 (■) | Comparison Formula (♦) |
|---|---|---|---|---|
| Amphetamine | 15 | 15 | 15 | 15 |
| Duro-Tak ® 87-9900 | 65 | 60 | 60 | — |
| Gelva ® GMS 3087 | 20 | 25 | — | 68 |
| Gelva ® GMS 9071 | — | — | 25 | — |
| Duro-Tak ® 900A | — | — | — | 17 |
| Coat Weight | 7.0 | 7.4 | 7.6 | 7 |
| (mg/cm²) |  |  |  |  |
| Backing | polyester | polyester | polyester | polyurethane/polyester |

Figure 2:
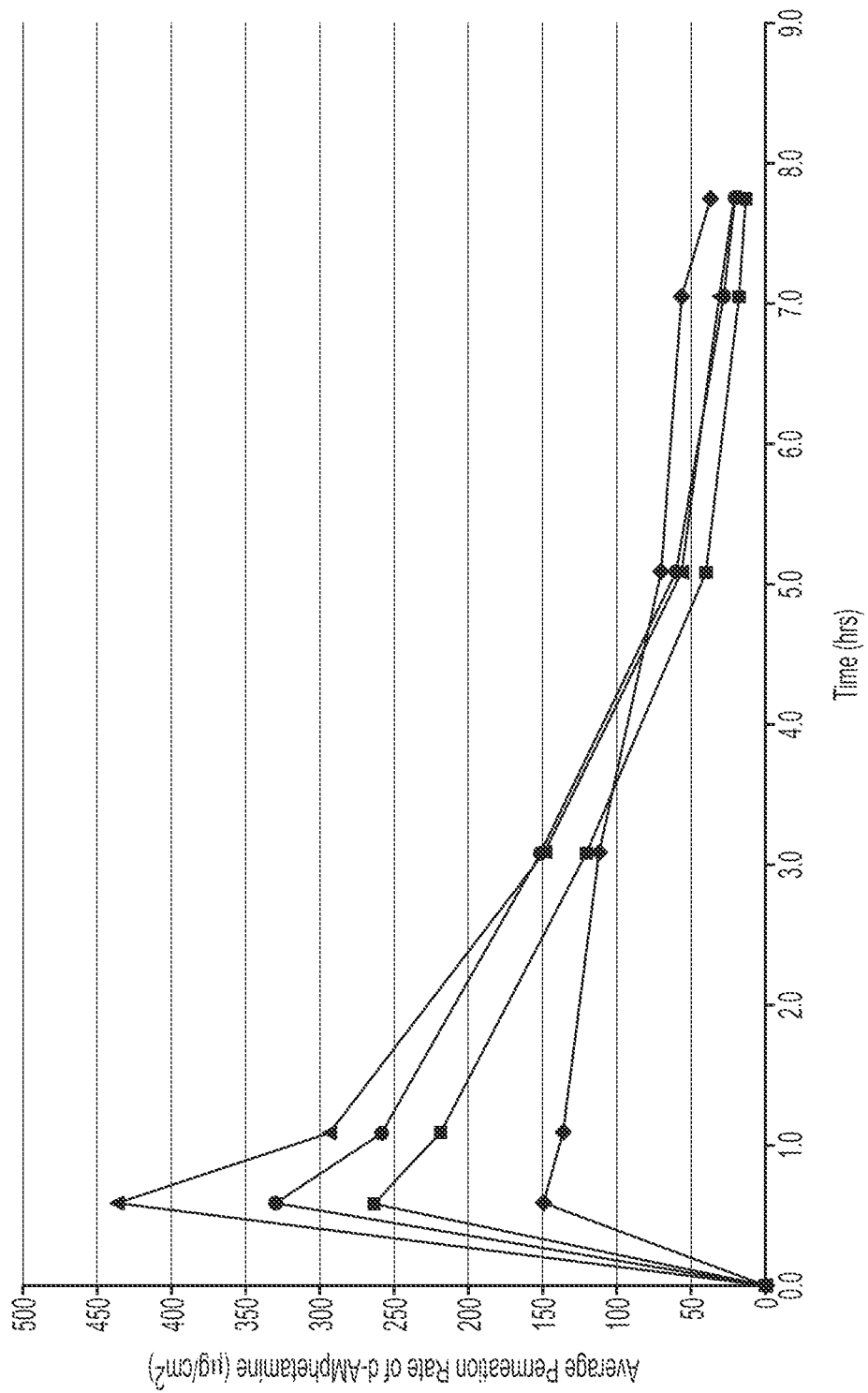
FIG. 2 illustrates the average drug flux ($\mu g/cm^2/hr$) from compositions as described herein and a comparison composition over 24 hours, as described in Example 2.

Drug flux from the systems over 24 hours was assessed in an in vitro assay using human cadaver skin. Results are shown in FIG. 2 (flux, μg/cm²/hr). As seen in the figures, compositions as described herein achieve more rapid drug flux than the comparison composition. Further, the drug flux can be selected and controlled by selecting and controlling the amount of ABC polymer and the type(s) and amount(s) of acrylic polymer(s).

Example 3

Systems were prepared using polymer matrix compositions with the following formulations, with coat weights of 5-7 mg/cm² and polyurethane/polyester backings:

|  | Formula 3-1 (Δ) | Formula 3-2 (♦) | Formula 3-3 (▲) | Formula 3-4 (●) | Comparison Formula (■) |
|---|---|---|---|---|---|
| Amphetamine | 10 | 10 | 15 | 12 | 15 |
| MMA/BA/AMS/PPG ABC | 53 | 30 | 25 | 28 | — |
| Duro-Tak ® 87-9900 | 35 | 30 | 30 | 30 | — |
| Gelva ® GMS 3087 | — | 30 | 30 | 30 | 67.5 |
| Duro-Tak ® 900A | — | — | — | — | 17.5 |

Figure 3:
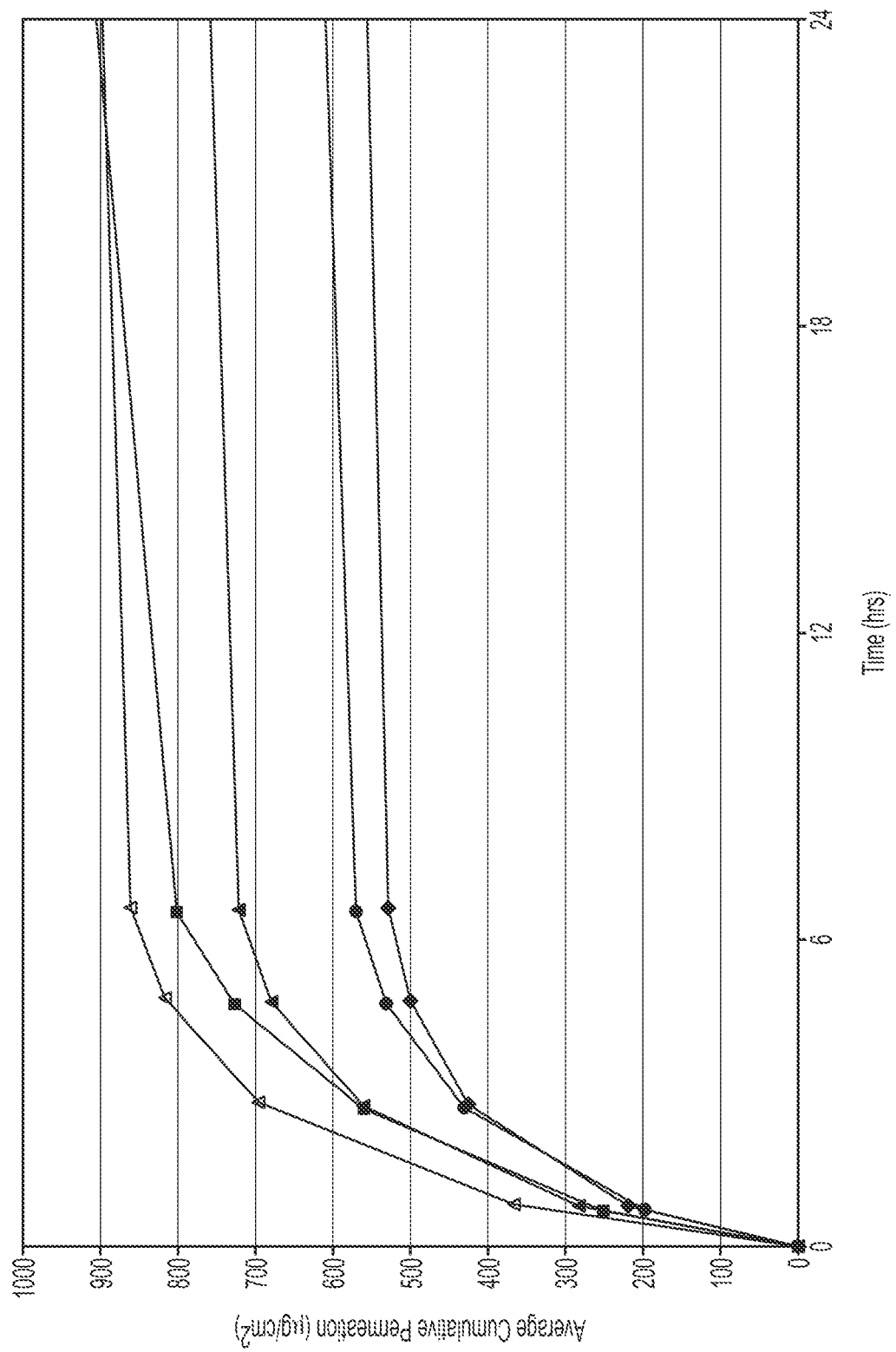
FIG. 3 illustrates the cumulative drug flux ($\mu g/cm^2$) from compositions as described herein and a comparison composition over 24 hours, as described in Example 3.

Drug flux from the systems over 24 hours was assessed in an in vitro assay using human cadaver skin. Results are shown in FIG. 3A (flux, μg/cm²/hr) and FIG. 3B (cumulative flux, μg/cm²). As seen in the figure, compositions as described herein achieve good drug flux, which can be selected and controlled by selecting and controlling the types and amounts of ABC polymer(s) and acrylic polymer(s). This figure also indicates that the compositions as described herein achieve a different flux profile than that of the comparison composition. For example, the comparison continues to deliver drug over the 24 hour period, while drug flux from the compositions described herein is substantially complete after 10 hours.

What is claimed is:

1. A composition for the transdermal delivery of amphetamine through skin in the form of a flexible finite system for topical application to skin, comprising a backing layer and a polymer matrix comprising amphetamine free base, wherein the polymer matrix comprises from about 20% to about 80% by weight of an acrylic block copolymer comprising two or more blocks made from monomers including an acrylic monomer, wherein the acrylic block copolymer comprises a block selected from the group consisting of a poly(butyl acrylate) block, a poly(methyl methacrylate) block, and a poly(butyl acrylate) block, wherein the composition is capable of transdermally delivering amphetamine through skin over a period of time of from about 6 to about 12 hours.

2. The composition of claim 1, wherein the polymer matrix further comprises a random acrylic polymer.

3. The composition of claim 2, wherein the random acrylic polymer is made from one or more monomers selected from the group consisting of butyl acrylate, methyl acrylate, acrylic acid, ethyl hexyl acrylate, and hydroxy ethyl acrylate.

4. The composition of claim 2, wherein the random acrylic polymer is made from one or more monomers selected from the group consisting of ethyl hexyl acrylate, methyl acrylate, butyl acrylate, and octyl acrylamide.

5. The composition of claim 1, wherein the polymer matrix comprises from about 10% to about 20% by weight amphetamine free base.

6. The composition of claim 5, wherein the polymer matrix comprises from about 25% to about 65% by weight acrylic block copolymer.

7. The composition of claim 5, wherein the polymer matrix comprises from about 10% to about 55% by weight random acrylic polymer.

8. The composition of claim 5, wherein the polymer matrix comprises from about 20% to about 30% by weight random acrylic polymer.

9. The composition of claim 1, wherein the composition is capable of transdermally delivering amphetamine through skin over a period of time of up to about 10 hours.

10. The composition according to claim 1, further comprising a release liner.

11. A method for the transdermal delivery of amphetamine through skin, comprising topically applying a composition as claimed in claim 1 to the skin or mucosa of a subject in need thereof.

12. A method of manufacturing a composition for the transdermal delivery of amphetamine through skin in the form of a flexible finite system for topical application to skin comprising a backing layer and a polymer matrix, comprising:

forming a polymer matrix blend comprising an acrylic block copolymer and amphetamine free base in a solvent, applying the polymer matrix blend to a backing layer, and removing any remaining solvent, wherein the acrylic block copolymer comprises two or more blocks made from monomers including an acrylic monomer, wherein the acrylic block copolymer comprises a block selected from the group consisting of a poly(butyl acrylate) block, a poly(methyl methacrylate) block, and a poly(butyl acrylate) block, and is present in an amount of from about 20% to about 80% by weight of the polymer matrix of the composition, wherein the composition is capable of transdermally delivering amphetamine through skin over a period of time of from about 6 to about 12 hours.

13. The composition of claim 1, wherein the acrylic block copolymer comprises a methyl methacrylate/butyl acrylate (MMA/BA) acrylic block copolymer.

14. The composition of claim 1, wherein the acrylic block copolymer comprises a methyl methacrylate/butyl acrylate/alpha methyl styrene/polypropylene glycol (MMA/BA/AMS/PPG) acrylic block copolymer.

* * * * *